(12) United States Patent
Zhao et al.

(10) Patent No.: US 12,094,612 B2
(45) Date of Patent: Sep. 17, 2024

(54) TUMOR DIAGNOSIS SYSTEM AND CONSTRUCTION METHOD THEREOF, TERMINAL DEVICE AND STORAGE MEDIUM

(71) Applicant: CANCER HOSPITAL, CHINESE ACADEMY OF MEDICAL SCIENCES, Beijing (CN)

(72) Inventors: Qing Zhao, Beijing (CN); Hongmei Zhang, Beijing (CN); Xinming Zhao, Beijing (CN)

(73) Assignee: CANCER HOSPITAL, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 18/385,407

(22) Filed: Oct. 31, 2023

(65) Prior Publication Data
US 2024/0062904 A1   Feb. 22, 2024

Related U.S. Application Data

(63) Continuation of application No. PCT/CN2022/114895, filed on Aug. 25, 2022.

(30) Foreign Application Priority Data

May 10, 2022  (CN) .......................... 202210502593.6

(51) Int. Cl.
  *G16H 50/20* (2018.01)
  *G06T 7/11* (2017.01)

(52) U.S. Cl.
  CPC .............. *G16H 50/20* (2018.01); *G06T 7/11* (2017.01); *G06T 2207/10081* (2013.01); *G06T 2207/20081* (2013.01); *G06T 2207/30028* (2013.01)

(58) Field of Classification Search
  CPC ........ G16H 50/20; G16H 30/40; G16H 50/30; G06T 7/11; G06T 2207/10081;
  (Continued)

(56) References Cited

U.S. PATENT DOCUMENTS

2017/0202633 A1* 7/2017 Liu .................. G16H 20/40
2019/0180153 A1* 6/2019 Buckler ............. G06F 18/29
(Continued)

FOREIGN PATENT DOCUMENTS

CN    109166105 A    1/2019
CN    111839445 A    10/2020
(Continued)

OTHER PUBLICATIONS

Liu Yuan, et al., Advances in the application of computer—aided diagnosis in colorectal cancer, Oncology Progress, 2009, pp. 267-271,285, vol. 7, No. 3.

*Primary Examiner* — Alexei Bykhovski
(74) *Attorney, Agent, or Firm* — Bayramoglu Law Offices LLC

(57) ABSTRACT

A tumor diagnosis system and a construction method thereof, a terminal device and a storage medium are provided, wherein a radiomics signature is obtained by a radiomics signature-generation module in the tumor diagnosis system according to target radiomics information and clinical data information, based on a pre-trained radiomics signature model; a first classification comprehensive diagnosis result is obtained by a benign and malignant comprehensive classification module according to a ambient situation of a lesion outside an intestinal wall, the clinical data information and a first radiomics signature, based on a pre-trained first classification comprehensive diagnosis model; a second classification comprehensive diagnosis result is generated through a malignant focus sub-classification module based on a pre-trained second classification
(Continued)

comprehensive diagnosis model, if the first classification comprehensive diagnosis result includes high-risk malignant information; and a final diagnosis result is obtained and displayed in a result displaying module.

5 Claims, 6 Drawing Sheets

(58) Field of Classification Search
CPC . G06T 2207/20081; G06T 2207/30028; G06T 2207/20084; G06T 2207/30096; G06T 7/0012; G06V 10/764; G06V 10/774
See application file for complete search history.

(56) References Cited

U.S. PATENT DOCUMENTS

| | | | |
|---|---|---|---|
| 2020/0160997 A1 | 5/2020 | Bagci et al. | |
| 2021/0038314 A1* | 2/2021 | Wibowo | A61B 18/04 |
| 2024/0047065 A1* | 2/2024 | Zennaro | G16H 50/20 |

FOREIGN PATENT DOCUMENTS

| | | | |
|---|---|---|---|
| CN | 112132917 A | | 12/2020 |
| CN | 113112449 A | | 7/2021 |
| CN | 113362893 A | | 9/2021 |
| CN | 113743463 A | * | 12/2021 |

* cited by examiner

TUMOR DIAGNOSIS SYSTEM AND CONSTRUCTION METHOD THEREOF, TERMINAL DEVICE AND STORAGE MEDIUM

CROSS REFERENCE TO RELATED APPLICATIONS

This application is a continuation application of International Application No. PCT/CN2022/114895, filed on Aug. 25, 2022, which claims priority to Chinese Patent Application No. 202210502593.6, filed on May 10, 2022, the entire contents of both of which are incorporated herein by reference.

TECHNICAL FIELD

The present disclosure relates to the field of medical technology, and in particular, to a tumor diagnosis system and a construction method thereof, a terminal device and a storage medium.

BACKGROUND

The incidence of colorectal cancer in China has been increasing year by year, and the prognosis is poor for advanced stage tumors. Early diagnosis and early treatment are key to reduce tumor burden and improve survival quality. The currently popular methods for screening intestinal cancer have low sensitivity and low specificity; although enteroscopy is considered as a gold standard, it is invasive, poorly tolerated, and has many contraindications, resulting in a low rate of early diagnosis and early treatment of intestinal cancer in China, and a heavy medical burden.

Therefore, it is necessary to propose a solution to reduce the difficulty of colorectal tumor screening and improve the effects on diagnosing colorectal tumors.

SUMMARY OF THE INVENTION

A main objective of the present disclosure is to provide a tumor diagnosis system and a construction method thereof, a terminal device and a storage medium, aiming at reducing the difficulty of colorectal tumor screening and meanwhile improving the diagnostic effect on colorectal tumors.

In order to achieve the aforementioned objective, the present disclosure provides a tumor diagnosis system, the tumor diagnosis system comprises:
  a radiomics signature-generation module for acquiring target radiomics information and clinical data information, and obtaining a radiomics signature according to the target radiomics information and the clinical data information, based on a pre-trained radiomics signature model, wherein the radiomics signature comprises a first radiomics signature and a second radiomics signature;
  a benign and malignant comprehensive classification module for acquiring an ambient situation of a lesion outside an intestinal wall, the clinical data information and the first radiomics signature, and generating a first classification comprehensive diagnosis result according to the ambient situation of the lesion outside the intestinal wall, the clinical data information and the first radiomics signature, based on a pre-trained first classification comprehensive diagnosis model;
  a malignant focus sub-classification module for acquiring the first classification comprehensive diagnosis result from the benign and malignant comprehensive classification module, and judging whether the first classification comprehensive diagnosis result comprises high-risk malignant information, if the first classification comprehensive diagnosis result comprises the high-risk malignant information, the ambient situation of the lesion outside the intestinal wall and the clinical data information are obtained from the benign and malignant comprehensive classification module, the second radiomics signature is obtained from the radiomics signature-generation module, and a second classification comprehensive diagnosis result is generated according to the ambient situation of the lesion outside the intestinal wall, the clinical data information and the second radiomics signature, based on a pre-trained second classification comprehensive diagnosis model;
  a result displaying module for acquiring the first classification comprehensive diagnosis result and/or the second classification comprehensive diagnosis result, obtaining a final diagnosis result according to the first classification comprehensive diagnosis result and/or the second classification comprehensive diagnosis result, and displaying the final diagnosis result for a user to check.

In an embodiment, the tumor diagnosis system further comprises:
  a CTC image preprocessing and reconstructing module for acquiring an enhanced CTC image of a patient to be diagnosed, and standardizing signal strength and layer thickness of the CTC image through a filter to obtain a preprocessed CTC image, and reconstructing the preprocessed CTC image based on a virtual endoscopy post-processing technology to obtain CT virtual endoscopic imaging for the user to conduct focus localization on the virtual endoscopic imaging and further obtain a focus localization image; and acquiring the focus localization image, and generating a CTC tomographic image according to the focus localization image.

In an embodiment, the tumor diagnosis system further comprises:
  a lesion marking module for acquiring the CTC tomographic image, recording the ambient situation of the lesion outside the intestinal wall according to the CTC tomographic image, and sending the ambient situation of the lesion outside the intestinal wall to the benign and malignant comprehensive classification module; providing the CTC tomographic image to the user for the user to delineate the CTC tomographic image layer by layer to obtain a region of interest; and acquiring the region of interest and sending the region of interest to a radiomics feature extraction module.

In an embodiment, the tumor diagnosis system further comprises:
  the radiomics feature extraction module for performing feature extraction on the region of interest to obtain the target radiomics information, and sending the target radiomics information to the radiomics signature-generation module.

In an embodiment, the tumor diagnosis system further comprises:
  a clinical data acquisition module for acquiring the clinical data information of the patient to be diagnosed input by the user, and sending the clinical data information to the radiomics signature-generation module, wherein the clinical data information comprises one or more of a gender, age, body mass index, family history of cancer, smoking history, constipation history, fecal occult blood and serological test result.

In an embodiment, the clinical data acquisition module further comprises a training sample data acquisition unit, and the training sample data acquisition unit is used for acquiring training sample data information input by the user and sending the training sample data information to a radiomics signature model training module, wherein the training sample data information comprises the clinical data information, colonoscopy and pathological information of a training set.

In an embodiment, the tumor diagnosis system further comprises: the radiomics signature model training module including a data cleaning unit, a logistic regression unit, and a signature vector calculation unit, wherein the data cleaning unit is used for acquiring an omics feature value and the training sample data information and performing data cleaning on the omics feature value and the training sample data information to obtain cleaned multi-omics feature data; the logistic regression unit is used for performing dimensionality reduction screening on the cleaned multi-omics feature data to obtain a first relevant radiomics feature and a second relevant radiomics feature; and the signature vector calculation unit is used for incorporating the first relevant radiomics feature and the second relevant radiomics feature into a vector formula to obtain the radiomics signature model.

In an embodiment, the tumor diagnosis system further comprises:
a first classification comprehensive diagnosis model training module for acquiring the training sample data information and the ambient situation of a lesion outside an intestinal wall of a training set, performing screening and analysis according to the training sample data information and the ambient situation of the lesion outside the intestinal wall of the training set to obtain a clinical risk factor; and performing training according to the clinical risk factor through a model training method to obtain the first classification comprehensive diagnosis model.

In an embodiment, in the tumor diagnosis system, the omics feature value comprises a first order feature, shape feature and/or textural feature of a lesion area. In an embodiment, the tumor diagnosis system further comprises:
a second classification comprehensive diagnosis model training module for judging whether the first classification comprehensive diagnosis result of the training set generated by the first classification comprehensive diagnosis model includes the high-risk malignant information, wherein if the first classification comprehensive diagnosis result of the training set includes the high-risk malignant information, the training sample data information and the ambient situation of the lesion outside the intestinal wall of the training set are acquired from the first classification comprehensive diagnosis model training module, and training is conducted in connection with a classification criteria according to the training sample data information and the ambient situation of the lesion outside the intestinal wall of the training set to obtain the second classification comprehensive diagnosis model.

In an embodiment, displayed contents of the result displaying module further comprises: a model structure nomogram and benign results generated by a benign and malignant comprehensive classification module, or a model structure nomogram and the malignant subclassification results generated by the malignant focus sub-classification module.

In an embodiment, an output end of the CTC image preprocessing and reconstructing module is connected to input ends of the lesion marking module, an output end of the lesion marking module is connected to input ends of the radiomics feature extraction module and the benign and malignant comprehensive classification module, output ends of the radiomics feature extraction module and the clinical data acquisition module are connected to an input end of the radiomics signature-generation module, output ends of the radiomics signature-generation module and the clinical data acquisition module are connected to an input end of the benign and malignant comprehensive classification module, output ends of the benign and malignant comprehensive classification module and the radiomics signature-generation module are connected to an input end of the malignant focus sub-classification module, output ends of the benign and malignant comprehensive classification module and the malignant focus sub-classification module are connected to an input end of the result displaying module.

Moreover, in order to achieve the aforementioned objective, the present disclosure also provides a method for constructing a tumor diagnosis system, the method for constructing a tumor diagnosis system includes:
establishing a radiomics signature model;
establishing a first classification comprehensive diagnosis model;
establishing a second classification comprehensive diagnosis model;
constructing a radiomics signature-generation module, a benign and malignant comprehensive classification module, a malignant focus sub-classification module, a result displaying module and module connections based on the radiomics signature model, the first classification comprehensive diagnosis model and the second classification comprehensive diagnosis model.

In an embodiment, the step of establishing a radiomics signature model includes:
acquiring an omics feature value and training sample data information;
performing data cleaning on the omics feature value and the training sample data information to obtain cleaned multi-omics feature data;
performing dimensionality reduction screening on the cleaned multi-omics feature data to obtain a first relevant radiomics feature and a second relevant radiomics feature;
incorporating the first relevant radiomics feature and the second relevant radiomics feature into a vector formula to obtain the radiomics signature model.

In an embodiment, the step of establishing a first classification comprehensive diagnosis model includes:
acquiring the training sample data information and the ambient situation of a lesion outside an intestinal wall of a training set;
performing screening and analysis according to the training sample data information and the ambient situation of the lesion outside the intestinal wall of the training set to obtain a clinical risk factor;
performing model training according to the clinical risk factor through a model training method to obtain the first classification comprehensive diagnosis model, wherein the model training method includes Decision Tree, Random Forest, Support Vector Machines, and Naive Bayes.

In an embodiment, the step of establishing a second classification comprehensive diagnosis model includes:

judging whether the first classification comprehensive diagnosis result of a training set generated by the first classification comprehensive diagnosis model includes high-risk malignant information;

acquiring the training sample data information and the ambient situation of the lesion outside the intestinal wall of the training set, if the first classification comprehensive diagnosis result of the training set includes the high-risk malignant information, and training, in connection with a classification criteria, according to the training sample data information and the ambient situation of the lesion outside the intestinal wall of the training set, to obtain the second classification comprehensive diagnosis model.

Moreover, in order to achieve the aforementioned objective, the present disclosure further provides a tumor diagnosis method, comprising:

acquiring target radiomics information and clinical data information, and obtaining a radiomics signature according to the target radiomics information and the clinical data information, based on a pre-trained radiomics signature model, wherein the radiomics signature comprises a first radiomics signature and a second radiomics signature;

acquiring an ambient situation of a lesion outside an intestinal wall, the clinical data information and the first radiomics signature, and generating a first classification comprehensive diagnosis result according to the ambient situation of the lesion outside the intestinal wall, the clinical data information and the first radiomics signature, based on a pre-trained first classification comprehensive diagnosis model;

judging whether the first classification comprehensive diagnosis result comprises high-risk malignant information, if the first classification comprehensive diagnosis result comprises the high-risk malignant information, generating a second classification comprehensive diagnosis result according to the ambient situation of the lesion outside the intestinal wall, the clinical data information and the second radiomics signature, based on a pre-trained second classification comprehensive diagnosis model;

obtaining a final diagnosis result according to the first classification comprehensive diagnosis result and/or the second classification comprehensive diagnosis result, and displaying the final diagnosis result for a user to check.

Moreover, in order to achieve the aforementioned objective, the present disclosure further provides an apparatus for tumor diagnosis, comprising:

a signature-generation module for acquiring target radiomics information and clinical data information, and obtaining a radiomics signature according to the target radiomics information and the clinical data information, based on a pre-trained radiomics signature model, wherein the radiomics signature comprises a first radiomics signature and a second radiomics signature;

a first classification module for acquiring an ambient situation of a lesion outside an intestinal wall, the clinical data information and the first radiomics signature, and generating a first classification comprehensive diagnosis result according to the ambient situation of the lesion outside the intestinal wall, the clinical data information and the first radiomics signature, based on a pre-trained first classification comprehensive diagnosis model;

a second classification module for judging whether the first classification comprehensive diagnosis result comprises high-risk malignant information, wherein if the first classification comprehensive diagnosis result comprises the high-risk malignant information, a second classification comprehensive diagnosis result is generated according to the ambient situation of the lesion outside the intestinal wall, the clinical data information and the second radiomics signature, based on a pre-trained second classification comprehensive diagnosis model;

a displaying module for obtaining a final diagnosis result according to the first classification comprehensive diagnosis result and/or the second classification comprehensive diagnosis result, and displaying the final diagnosis result for a user to check.

Moreover, in order to achieve the aforementioned objective, the present disclosure further provides a terminal device, which includes a memory, a processor, and a tumor diagnosis system construction program stored in the memory and operable on the processor, wherein when executed by the processor, the tumor diagnosis system construction program implements the steps of the method for constructing a tumor diagnosis system as described above.

Moreover, in order to achieve the aforementioned objective, the present disclosure further provides a computer-readable storage medium on which a tumor diagnosis system construction program is stored, wherein when executed by a processor, the tumor diagnosis system construction program implements the steps of the method for constructing a tumor diagnosis system as described above.

For the tumor diagnosis system and a construction method thereof, the terminal device and the storage medium proposed by the embodiments of the present disclosure, target radiomics information and clinical data information are acquired through a radiomics signature-generation module in the tumor diagnosis system, and a radiomics signature is obtained based on a pre-trained radiomics signature model and according to the target radiomics information and the clinical data information; a first classification comprehensive diagnosis result is generated through a benign and malignant comprehensive classification module, based on a pre-trained first classification comprehensive diagnosis model and according to a ambient situation of a lesion outside an intestinal wall, the clinical data information and the first radiomics signature; whether the first classification comprehensive diagnosis result includes high-risk malignant information is judged through a malignant focus sub-classification module, and if the first classification comprehensive diagnosis result includes the high-risk malignant information, a second classification comprehensive diagnosis result is judged based on a pre-trained second classification comprehensive diagnosis model and according to the ambient situation of the lesion outside the intestinal wall, the clinical data information and the second radiomics signature; and a final diagnosis result is obtained and displayed through a result displaying module. it achieves comprehensive diagnosis which combines radiomics and clinical information, which can not only identify the benign and malignant of suspicious lesions, but also further reclassify malignant lesions, so as to help clinicians make further decisions, without the need for colonoscopy in the whole process, thereby reducing the screening difficulty of colorectal tumors and simultaneously improving the diagnostic effect on the colorectal tumors.

Figure 1:
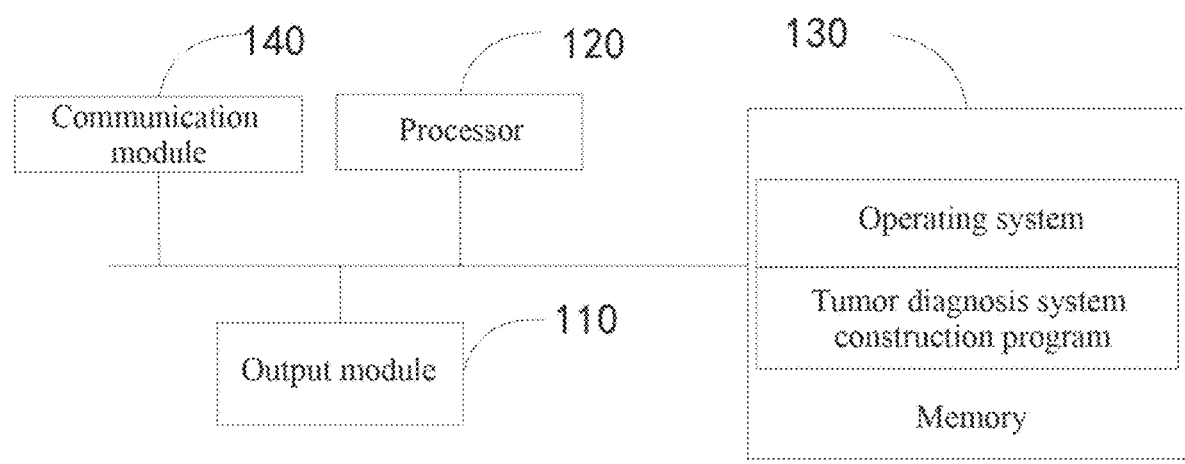
FIG. 1 is a schematic diagram of functional modules of a terminal device to which an apparatus corresponding to a method for constructing a tumor diagnosis system of the present disclosure belongs.

The realization of the objective, functional characteristics and advantages of the present disclosure will be further described in conjunction with embodiments and with reference to the accompanying drawings.

DETAILED DESCRIPTION OF THE EMBODIMENTS

It should be understood that the specific examples described herein are only used for explaining the present disclosure, and are not used for limiting the present disclosure.

The main solution of the embodiments of the present disclosure is that, by: acquiring target radiomics information and clinical data information through a radiomics signature-generation module in the tumor diagnosis system, and obtaining a radiomics signature based on a pre-trained radiomics signature model and according to the target radiomics information and the clinical data information; generating a first classification comprehensive diagnosis result through a benign and malignant comprehensive classification module based on a pre-trained first classification comprehensive diagnosis model and based on a ambient situation of a lesion outside an intestinal wall, the clinical data information and the first radiomics signature; judging whether the first classification comprehensive diagnosis result includes high-risk malignant information through a malignant focus sub-classification module, and generating a second classification comprehensive diagnosis result based on a pre-trained second classification comprehensive diagnosis model and according to the ambient situation of the lesion outside the intestinal wall, the clinical data information and the second radiomics signature, if the first classification comprehensive diagnosis result includes the high-risk malignant information; and obtaining and displaying a final diagnosis result through a result displaying module, it achieves comprehensive diagnosis which combines radiomics and clinical information, which can not only identify benign and malignant suspicious lesions, but also further reclassify malignant lesions, so as to help clinicians make further decisions, without the need for colonoscopy in the whole process, thereby reducing the screening difficulty of colorectal tumors and improving the diagnostic effect on the colorectal tumors simultaneously.

Technical terms involved in the embodiments of the present disclosure:
Electron Computed Tomography: Computed Tomography, CT;
CT virtual colonoscopy: CT colonoscopy, CTC;
Computer-aided diagnosis: computer-aided diagnosis, CAD;
Virtual Endoscopy: Virtual Endoscopy, VE;
Region of interest: region of interest, ROI;
Gray-level co-occurrence matrices: Gray-level co-occurrence matrices, GLCM;
Gray-level run length matrix: Gray-level run length matrix, GLRLM;
Gray-level size zone matrix: Gray-level size zone matrix, GLSZM;
Gray level dependence matrix: Gray level dependence matrix, GLDM.

The incidence of colorectal cancer in China is increasing year by year, and the prognosis is poor for advanced tumors. Early diagnosis and early treatment are key to reduce tumor burden and improve survival quality. The currently popular methods for screening intestinal cancer have low sensitivity and low specificity; although enteroscopy is considered as a gold standard, it is invasive, poorly tolerated, and has many contraindications, resulting in a low rate of early diagnosis and early treatment of intestinal cancer in China and a heavy medical burden. Therefore, it is imperative to improve colorectal cancer screening technology and build a safe and accurate screening system. CT Colonography (CTC) has the characteristics such as non-invasive, convenient, accurate, and having few contraindications, can reflect information inside and outside the intestinal tract at the same time, and is the most ideal screening method for intestinal cancer. However, in the prior art, there still exists the disadvantages of low detection rate of small focuses, high false positive rate and low diagnostic accuracy at the same time. Although currently there are researches that combine radiomics features, machine learning and deep learning computer-aided diagnosis (CAD) devices, the constructed diagnostic model is only based on the image itself and lacks comprehensive diagnosis of clinical information, leading to still low accuracy. On the other hand, the diagnosis only stays at the level of distinguishing between "benign and malignant", for suspicious malignant lesions, how to further group them to facilitate the next decision-making has not been realized by the current technology.

The present disclosure provides a solution to construct a system for performing semi-automatic diagnosis of colorectal tumors under supervision (manually delineating a focus rather than CAD automatic recognition) on a main basis of radiomics analysis of CT colonoscopy (CTC) combined with clinical information, mainly aiming at the disadvantages of the prior art in simply analyzing images but ignoring the auxiliary significance of the clinical information for screening, lacking further prompts for suspicious malignant lesions, and being not comprehensive enough for clinical decision-making. This system not only identify the benign (a normal intestinal wall or hyperplastic polyps) and malignant (precancerous lesions or cancer) of suspicious lesions, but also further reclassify the malignant lesions (the precancerous lesions, a cancer below T1N0, and a staged cancer above T1N0), to help clinicians make further decisions.

Specifically, referring to FIG. 1, it is a schematic diagram of functional modules of a terminal device to which an apparatus corresponding to a method for constructing a tumor diagnosis system of the present disclosure belongs. The apparatus may be an apparatus independent of the terminal device and capable of performing the construction of a tumor diagnosis system. It may be carried on the terminal device in a form of hardware or software. The terminal device may be an intelligent mobile terminal with a data processing function, such as a mobile phone, a tablet computer and the like, or may be a fixed terminal device or a server with a data processing function.

In present embodiments, the terminal device to which the apparatus for constructing the tumor diagnosis system belongs includes at least an output module 110, a processor 120, a memory 130 and a communication module 140.

The memory 130 stores an operating system and a tumor diagnosis system construction program. The apparatus for constructing the tumor diagnosis system can stores information, such as a radiomics signature model, a first classification comprehensive diagnosis model, a second classification comprehensive diagnosis model, a radiomics signature-generation module, a benign and malignant comprehensive classification module, a malignant focus sub-classification module, a result displaying module and module connections constructed based on the radiomics signature model, the first classification comprehensive diagnosis model and the second classification comprehensive diagnosis model, and the like in the memory 130. The output module 110 may be a display screen or the like. The communication module 140 may include a WIFI module, a mobile communication module, and a Bluetooth module, etc., and communication with an external device or server is conducted through the communication module 140.

When executed by the processor, the tumor diagnosis system construction program in the memory 130 implements the following steps:
 establishing a radiomics signature model;
 establishing a first classification comprehensive diagnosis model;
 establishing a second classification comprehensive diagnosis model;
 constructing a radiomics signature-generation module, a benign and malignant comprehensive classification module, a malignant focus sub-classification module, a result displaying module and module connections based on the radiomics signature model, the first classification comprehensive diagnosis model and the second classification comprehensive diagnosis model.

In an embodiment, when executed by the processor, the tumor diagnosis system construction program in the memory 130 further implements the following steps:
 acquiring an omics feature value and training sample data information;
 performing data cleaning on the omics feature value and the training sample data information to obtain cleaned multi-omics feature data;
 performing dimensionality reduction screening on the cleaned multi-omics feature data to obtain a first relevant radiomics feature and a second relevant radiomics feature;
 incorporating the first relevant radiomics feature and the second relevant radiomics feature into a vector formula to obtain the radiomics signature model.

In an embodiment, when executed by the processor, the tumor diagnosis system construction program in the memory 130 further implements the following steps:
 acquiring the training sample data information and the ambient situation of a lesion outside an intestinal wall of a training set;
 performing screening and analysis according to the training sample data information and the ambient situation of the lesion outside the intestinal wall of a training set to obtain a clinical risk factor; and
 performing model training according to the clinical risk factor through a model training method to obtain the first classification comprehensive diagnosis model, wherein the model training method includes Decision Tree, Random Forest, Support Vector Machines, and Naive Bayes.

In an embodiment, when executed by the processor, the tumor diagnosis system construction program in the memory 130 further implements the following steps:
 is judging whether the first classification comprehensive diagnosis result of a training set generated by the first classification comprehensive diagnosis model includes high-risk malignant information; and
 acquiring the training sample data information and the ambient situation of the lesion outside the intestinal wall of the training set, and training in connection with a classification criteria according to the training sample data information and the ambient situation of the lesion outside the intestinal wall of the training set to obtain the second classification comprehensive diagnosis model, if the first classification comprehensive diagnosis result of the training set includes the high-risk malignant information.

In the present embodiments, through the aforementioned solutions, specifically, by establishing a radiomics signature model; establishing a first classification comprehensive diagnosis model; establishing a second classification comprehensive diagnosis model; and constructing a radiomics signature-generation module, a benign and malignant comprehensive classification module, a malignant focus sub-classification module, a result displaying module and module connections, based on the radiomics signature model, the first classification comprehensive diagnosis model and the second classification comprehensive diagnosis model. A system for performing semi-automatic diagnosis of colorectal tumors under supervision (manually delineating a focus instead of CAD automatic recognition) is constructed on a main basis of radiomics analysis of CT colonoscopy (CTC) combined with clinical information. This system can not only identify the benign (a normal intestinal wall or hyperplastic polyps) and malignant (precancerous lesions or cancer) of suspicious lesions, but also reclassify the malignant lesions (the precancerous lesions, the cancer below T1N0, and the staged cancer above T1N0), to help clinicians make further decisions.

Figure 2:
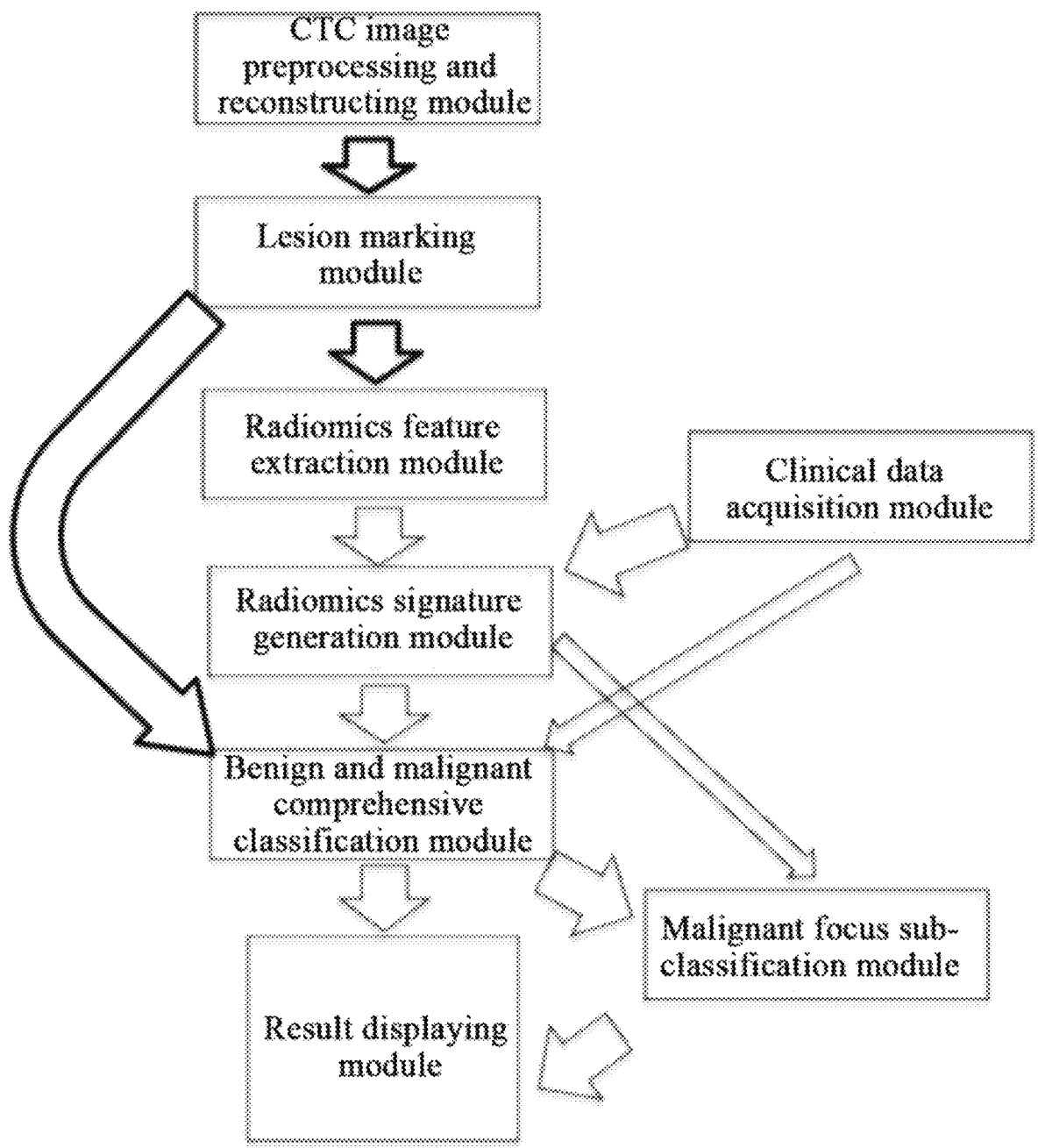
FIG. 2 is a schematic diagram of a basic architecture of the tumor diagnosis system of the present disclosure.

Based on, but not limited to the aforementioned terminal device architecture, the present disclosure provides a tumor diagnosis system. Referring to FIG. 2, it is a schematic diagram of a basic architecture of the tumor diagnosis system of the present disclosure. In an embodiment of the tumor diagnosis system of the present disclosure, the tumor diagnosis system includes:
 a radiomics signature-generation module for acquiring target radiomics information and clinical data information, and obtaining a radiomics signature according to the target radiomics information and the clinical data information, based on a pre-trained radiomics signature model, wherein the radiomics signature includes a first radiomics signature and a second radiomics signature;
 a benign and malignant comprehensive classification module for acquiring an ambient situation of a lesion outside an intestinal wall, the clinical data information and the first radiomics signature, and generating a first classification comprehensive diagnosis result according to the ambient situation of the lesion outside the intestinal wall, the clinical data information and the first radiomics signature, based on a pre-trained first classification comprehensive diagnosis model;

a malignant focus sub-classification module for acquiring the first classification comprehensive diagnosis result from the benign and malignant comprehensive classification module, and judging whether the first classification comprehensive diagnosis result includes high-risk malignant information, wherein if the first classification comprehensive diagnosis result includes the high-risk malignant information, the ambient situation of the lesion outside the intestinal wall and the clinical data information are obtained from the benign and malignant comprehensive classification module, the second radiomics signature is obtained from the radiomics signature-generation module, and a second classification comprehensive diagnosis result is generated according to the ambient situation of the lesion outside the intestinal wall, the clinical data information and the second radiomics signature, based on a pre-trained second classification comprehensive iii diagnosis model; and a result displaying module for acquiring the first classification comprehensive diagnosis result and/or the second classification comprehensive diagnosis result, obtaining a final diagnosis result according to the first classification comprehensive diagnosis result and/or the second classification comprehensive diagnosis result, and displaying the final diagnosis result for a user to check.

In an embodiment, the tumor diagnosis system further includes:

a CTC image preprocessing and reconstructing module for acquiring an enhanced CTC image of a patient to be diagnosed, and standardizing signal strength and layer thickness of the CTC image through a filter to obtain a preprocessed CTC image, and reconstructing the preprocessed CTC image based on a virtual endoscopy post-processing technology to obtain CT virtual endoscopic imaging for the user to conduct focus localization on the virtual endoscopic imaging and further obtain a focus localization image; and acquiring the focus localization image, and generating a CTC tomographic image according to the focus localization image;

a lesion marking module for acquiring the CTC tomographic image, recording the ambient situation of the lesion outside the intestinal wall according to the CTC tomographic image, and sending the ambient situation of the lesion outside the intestinal wall to the benign and malignant comprehensive classification module; providing the CTC tomographic image to the user for the user to delineate the CTC tomographic image layer by layer to obtain a region of interest; and acquiring the region of interest and sending the region of interest to a radiomics feature extraction module;

the radiomics feature extraction module for performing feature extraction on the region of interest to obtain the target radiomics information, and sending the target radiomics information to the radiomics signature-generation module; and a clinical data acquisition module for acquiring the clinical data information of the patient to be diagnosed input by the user, and sending the clinical data information to the radiomics signature-generation module, wherein the clinical data information includes one or more of a gender, age, body mass index, family history of cancer, smoking history, constipation history, fecal occult blood and serological test result.

Still further, the clinical data acquisition module further includes a training sample data acquisition unit, and the training sample data acquisition unit is used for acquiring training sample data information input by the user and sending the training sample data information to a radiomics signature model training module, wherein the training sample data information includes clinical data information, colonoscopy and pathological information of training sets.

In an embodiment, the tumor diagnosis system further includes:

a radiomics signature model training module including a data cleaning unit, a logistic regression unit, and a signature vector calculation unit, wherein the data cleaning unit is used for acquiring an omics feature value and the training sample data information and performing data cleaning on the omics feature value and the training sample data information to obtain cleaned multi-omics feature data; the logistic regression unit is used for performing dimensionality reduction screening on the cleaned multi-omics feature data to obtain a first relevant radiomics feature and a second relevant radiomics feature; the signature vector calculation unit is used for incorporating the first relevant radiomics feature and the second relevant radiomics feature into a vector formula to obtain the radiomics signature model;

a first classification comprehensive diagnosis model training module for acquiring the training sample data information and the ambient situation of a lesion outside an intestinal wall of a training set, performing screening and analysis according to the training sample data information and the ambient situation of the lesion outside the intestinal wall of a training set to obtain a clinical risk factor; and performing training according to the clinical risk factor through a model training method to obtain the first classification comprehensive diagnosis model;

a second classification comprehensive diagnosis model training module for judging whether a first classification comprehensive diagnosis result of a training set generated by the first classification comprehensive diagnosis model includes the high-risk malignant information, wherein if the first classification comprehensive diagnosis result of a training set includes the high-risk malignant information, the training sample data information and the ambient situation of the lesion outside the intestinal wall of the training set are acquired from the first classification comprehensive diagnosis model training module, and training is conducted in connection with a classification criteria according to the training sample data information and the ambient situation of the lesion outside the intestinal wall of the training set to obtain the second classification comprehensive diagnosis model.

Specifically, a process of performing diagnosis using the tumor diagnosis system according to the embodiments of the present disclosure particularly includes the follows:

an enhanced CTC (venous phase) image of a patient to be diagnosed and clinical data information are input into a clinical data acquisition module, wherein the clinical data information includes a gender, age, body mass index, family history of cancer, smoking history, constipation history, fecal occult blood and serological test result (CEA, CA-199 levels), etc. The signal intensity and layer thickness (1 mm) are standardized by a CTC image preprocessing and reconstructing module through a filter, and a CTVE image is obtained by reconstructing using a virtual endoscopy (VE) post-processing technology. The whole colon condition is observed by an operator in the CTVE image and a suspicious focus is marked and localized, the module automatically outputs a CTC two-dimensional panoramic image, excluding the image information outside the marked range.

In an embodiment, in the lesion marking module, based on the CTC tomographic image output by the CTC image preprocessing and reconstructing module and by using ITK-SNAP software, the operator delineates a region of interest (ROI) representing a tumor tissue layer by layer to avoid from necrosis and a normal intestinal wall tissue, and outputs the delineated ROI to the radiomics feature extraction module. At the same time, the module also needs to record the ambient situation of a lesion outside an intestinal wall, for the operator to evaluate whether there is extraintestinal infiltration (manifested as that the outer edge of the intestinal wall is not smooth, the boundary is not clear, and the density of mesenteric fat is increased than that of a non-lesion region), and a lymph node having a drainage region short diameter greater than 1 cm, etc., which is output to the benign and malignant comprehensive classification module. The radiomics feature extraction module is responsible for extracting a relevant radiomics feature value based on the ROI in the CTC tomographic image input by the image preprocessing module. In the embodiments of the present disclosure, 707 feature values are included to describe the first-order features (19), shape features (16) and texture features (28 GLCMs, 16 GLRLMs, 16 GLSZMs, 18 GLDMs, 269 Wavelets and 325 Logs) of the focus region, respectively.

In an embodiment, the radiomics signature-generation module is mainly based on the omics feature value input by the radiomics feature extraction module and the clinical data information input by the clinical data acquisition module, based on the pre-screened and constructed radiomics signatures (Sig1 and Sig2) capable of performing accurate dichotomy, a radiomics signature (Sig1) for distinguishing benign (folds, hyperplastic polyps) from malignant (adenomas, adenocarcinomas) lesions, and a radiomics signature (Sig2) for distinguishing precancerous lesions, adenocarcinomas below T1 and adenocarcinomas above T1.

The benign and malignant comprehensive classification module will acquire the clinical information of a patient acquired by the clinical data acquisition module and the ambient situation of the lesion outside the intestinal wall input by the lesion marking module, for example the peritoneum and lymph node condition of a lesion outside an intestinal cavity; and generate a first classification comprehensive diagnosis model based on a first classification comprehensive diagnosis model (model 1) generated by pre-training in combination with the radiomics signature Sig1.

The malignant focus sub-classification module acquires the first classification comprehensive diagnosis result from the benign and malignant comprehensive classification module, and judges whether the first classification comprehensive diagnosis result includes a result having a score greater than 140 and a malignant risk greater than 75%, if included, it is determined as the high-risk malignant information, and it is necessary to acquire the ambient situation of the lesion outside the intestinal wall and the clinical data information from the benign and malignant comprehensive classification module, acquire a second radiomics signature from the radiomics signature-generation module, and generate a second classification comprehensive diagnosis result based on a pre-trained second classification comprehensive diagnosis model (model 2) and according to the ambient situation of the lesion outside the intestinal wall, the clinical data information and the second radiomics signature.

According to the benign or malignant output of the benign and malignant comprehensive classification module, the displayed contents of the result displaying module will be selected respectively from a model structure nomogram and a benign result from the benign and malignant comprehensive classification module, or the model structure nomogram and a malignant sub-classification result from the malignant focus sub-classification module, and a characteristic curve operated on a receiver and obtained in advance that represents the predictive performance of the model. Further, according to the prospective case information (the CTT image and the clinical data) to be predicted as input by the operator subsequently, the system will display the corresponding Sig1 and Sig2 scores, the total scores of models 1 and 2 and a final diagnosis result (benign or malignant sub-classification condition) according to the aforementioned nomogram.

In the present embodiments, through the aforementioned solutions, specifically by acquiring target radiomics information and clinical data information through a radiomics signature-generation module, and obtaining a radiomics signature based on a pre-trained radiomics signature model and according to the target radiomics information and the clinical data information; generating a first classification comprehensive diagnosis result through a benign and malignant comprehensive classification module based on a pre-trained first classification comprehensive diagnosis model and based on a ambient situation of a lesion outside an intestinal wall, the clinical data information and the first radiomics signature; judging whether the first classification comprehensive diagnosis result includes high-risk malignant information through a malignant focus sub-classification module, and generating a second classification comprehensive diagnosis result based on a pre-trained second classification comprehensive diagnosis model and according to the ambient situation of the lesion outside the intestinal wall, the clinical data information and the second radiomics signature, if the first classification comprehensive diagnosis result includes the high-risk malignant information; and obtaining and displaying a final diagnosis result through a result displaying module, it achieves comprehensive diagnosis which combines radiomics and clinical information, which can not only identify the benign and malignant of suspicious lesions, but also reclassify malignant lesions, so as to help clinicians make further decisions, without the need for colonoscopy in the whole process, thereby reducing the screening difficulty of colorectal tumors and improving the diagnostic effect on the colorectal tumors simultaneously.

In the present embodiments, an executive body of the method for constructing a tumor diagnosis system may be an apparatus or a terminal device for constructing a tumor diagnosis system, etc. The present embodiments take the apparatus for constructing a tumor diagnosis system as an example.

Figure 3:
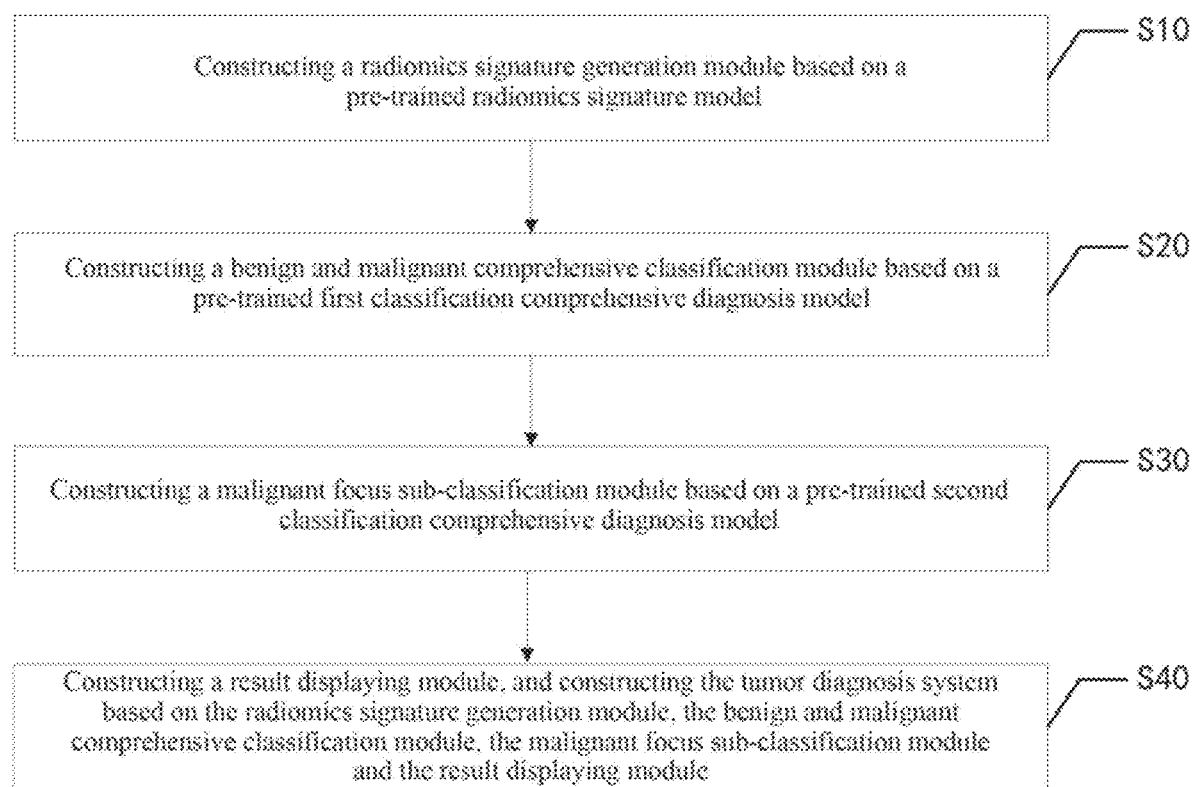
FIG. 3 is a schematic flow chart of an exemplary embodiment of the method for constructing a tumor diagnosis system of the present disclosure.

Referring to FIG. 3, it is a schematic flow chart of an exemplary embodiment of the method for constructing a tumor diagnosis system of the present disclosure. The method for constructing a tumor diagnosis system comprises the following steps.

Step S10, a radiomics signature-generation module is constructed based on a pre-trained radiomics signature model.

Prior to this step, it is necessary to obtain the radiomics signature model through training. The specific step comprises:

acquiring an omics feature value and training sample data information;

performing data cleaning on the omics feature value and the training sample data information to obtain cleaned multi-omics feature data;

performing dimensionality reduction screening on the cleaned multi-omics feature data to obtain a first relevant radiomics feature and a second relevant radiomics feature;

incorporating the first relevant radiomics feature and the second relevant radiomics feature into a vector formula to obtain the radiomics signature model.

Specifically, based on the omics feature value input by the radiomics feature extraction module and the colonoscopy and pathological information input by the clinical data acquisition module, the radiomics signature (Sig1) for distinguishing benign (folds, hyperplastic polyps) from malignant (adenomas, adenocarcinomas) lesions, and the radiomics signature (Sig2) for distinguishing precancerous lesions, adenocarcinomas below T1 and adenocarcinomas above T1, are screened out and constructed respectively. This part is mainly divided into three steps, including data cleaning, logistic regression and signature vector calculation. The data cleaning is mainly responsible for cleaning out invalid data and erroneous data in the multi-omics feature data, and meanwhile transforming a continuous variable into a dichotomous variable with a median as a margin value. The logistic regression is responsible for performing dimensionality reduction screening of the multi-omics feature data, and will conduct data dimensionality reduction on the radiomics variables respectively based on a relationship between the omics feature and the classification and by using the least absolute shrinkage and a selection operator formula in R software, to screen out a radiomics feature with significant correlations ($p<0.05$) with the benign and malignant classification and the malignant sub-classification. The signature vector calculation is responsible for incorporating the aforementioned radiomics feature into a vector formula by using a machine learning method to form radiomics signatures (Sig1 and Sig2) that can conduct accurate dichotomy, so as to further obtain a radiomics signature-generation module.

Step S20, a benign and malignant comprehensive classification module is constructed based on a pre-trained first classification comprehensive diagnosis model.

Prior to this step, it is necessary to obtain the first classification comprehensive diagnosis model through training. The specific step comprises:

acquiring the training sample data information and the ambient situation of a lesion outside an intestinal wall of a training set;

performing screening and analysis according to the training sample data information and the ambient situation of the lesion outside the intestinal wall of the training set to obtain a clinical risk factor;

performing model training according to the clinical risk factor through a model training method to obtain the first classification comprehensive diagnosis model, wherein the model training method comprises Decision Tree, Random Forest, Support Vector Machines, and Naive Bayes.

Specifically, screening is conducted on the clinical information of the patient acquired by the clinical data acquisition module and the peritoneum and lymph node condition of the lesion outside the intestinal cavity input by the lesion marking module, by using univariate regression analysis in SPSS software to find out clinical and traditional image risk factors that can significantly distinguish benign and malignant lesions ($P<0.05$), and multivariate regression analysis is conducted in combination with the radiomics signature Sig1 to obtain a clinical risk factor that can significantly and independently distinguish benign and malignant lesions ($P<0.05$), so as to further select the best machine learning model in the system (including, but not limited to Decision Tree, Random Forest, Support Vector Machines, Naive Bayes, etc.). In the embodiments of the present disclosure, the model construction method with the highest performance as selected during model construction is the support vector machine method. In turn, a benign and malignant classification comprehensive diagnosis model 1 with the highest accuracy and stability, i.e., the first classification comprehensive diagnosis model, is generated. Based on this model, a benign and malignant comprehensive classification module can be composed to identify the benign (a normal intestinal wall or hyperplastic polyps) and malignant (precancerous lesion or cancer) of a suspicious lesion.

Step S30. a malignant focus sub-classification module is construct based on a pre-trained second classification comprehensive diagnosis model.

Prior to this step, it is necessary to obtain the second classification comprehensive diagnosis model through training. The specific step comprises:

judging whether the first classification comprehensive diagnosis result of a training set generated by the first classification comprehensive diagnosis model comprises high-risk malignant information; and acquiring the training sample data information and the ambient situation of the lesion outside the intestinal wall of a training set, and training in connection with a classification criteria according to the training sample data information and the ambient situation of the lesion outside the intestinal wall of the training set to obtain the second classification comprehensive diagnosis model, if the first classification comprehensive diagnosis result of the training set includes the high-risk malignant information.

Specifically, according to the high-risk malignant output by the benign and malignant comprehensive classification module (having a score greater than 140 and a malignant risk greater than 75% in the model 1), the traditional image and clinical information in this module are further extracted, and meanwhile the Sig2 in the radiomics signature-generation module is extracted. According to the classification criteria for adenomas as well as adenomas below T1N0 and adenomas above T1N0, and by using the SPSS software again, univariate and multivariate analysis are conducted in sequence, to further select the best machine learning model in the system (including, but not limited to Decision Tree, Random Forest, Support Vector Machines, Naive Bayes, etc.). In the embodiments of the present disclosure, the model construction method with the highest performance as selected during model construction is the support vector machine method. In turn, a classification comprehensive diagnosis model 2 with the highest accuracy and stability, i.e., the second classification comprehensive diagnosis model, is generated. Based on this model, a malignant focus sub-classification module can be composed to reclassify the malignant lesions, e.g., a precancerous lesion, a cancer below T1N0 and a staged cancer above T1N0.

Step S40. a result displaying module is constructed, and the tumor diagnosis system is constructed based on the radiomics signature-generation module, the benign and malignant comprehensive classification module, the malignant focus sub-classification module and the result displaying module.

Specifically, the tumor diagnosis system is obtained by constructing a CTC image preprocessing and reconstructing module, a lesion marking module, a radiomics feature extraction module, a clinical data acquisition module, a benign and malignant comprehensive classification module, a malignant focus sub-classification module, and a result displaying module. An output end of the CTC image preprocessing and reconstructing module is connected to an input end of the lesion marking module. An output end of the lesion marking module is connected to input ends of the radiomics feature extraction module and the benign and malignant comprehensive classification module. Output ends of the radiomics feature extraction module and the clinical data acquisition module are connected to an input end of the radiomics signature-generation module. Output ends of the radiomics signature-generation module and the clinical data acquisition module are connected to an input end of the benign and malignant comprehensive classification module. Output ends of the benign and malignant comprehensive classification module and the radiomics signature-generation module are connected to an input end of the malignant focus sub-classification module. Output ends of the benign and malignant comprehensive classification module and the malignant focus sub-classification module are connected to an input end of the result displaying module.

Figure 4:
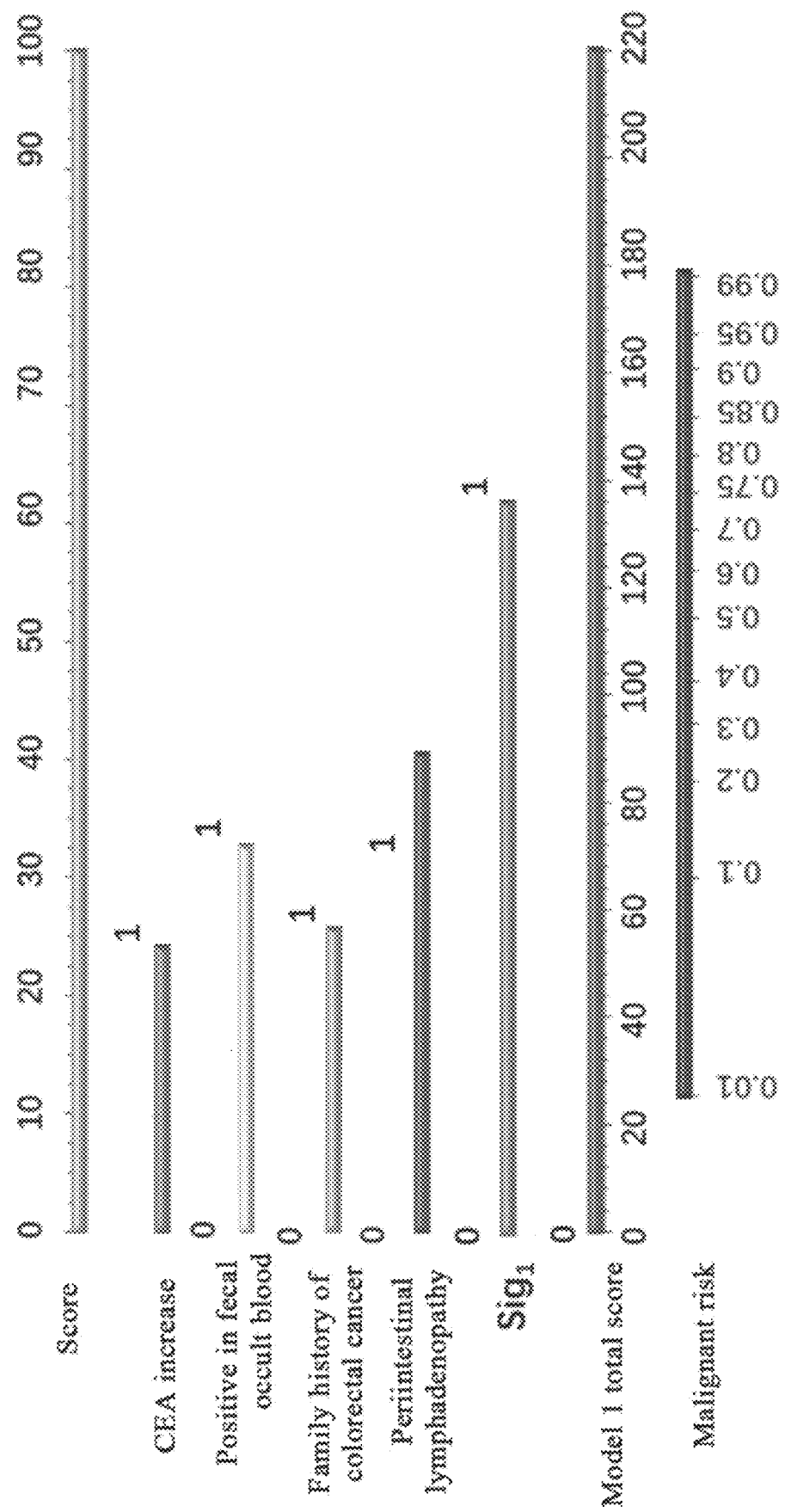
FIG. 4 is a nomogram of a first classification comprehensive diagnosis model in an embodiment of the present disclosure.
Figure 5:
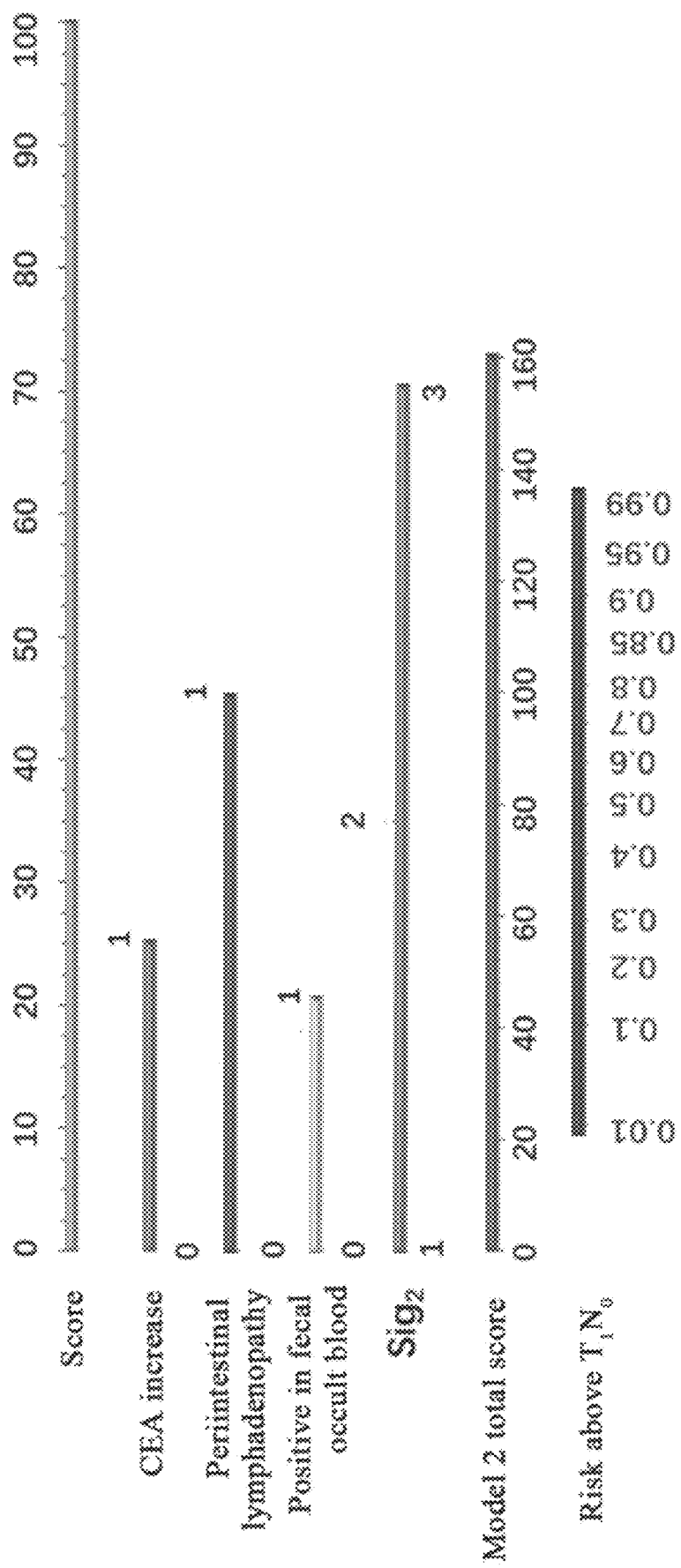
FIG. 5 is a nomogram of a second classification comprehensive diagnosis model in an embodiment of the present disclosure.

Referring to FIGS. 4 and 5, they are respectively a nomogram of the first classification comprehensive diagnosis model of the embodiments of the present disclosure and a nomogram of the second classification comprehensive diagnosis model of the embodiments of the present disclosure. After the tumor diagnosis system is obtained, the system can be verified through a verification set. In the embodiments of the present disclosure, based on the clinical, imaging and pathological data of 960 asymptomatic high-risk populations, a semi-automatic diagnosis system for colorectal tumors is constructed and externally verified based on the CT virtual colonoscopy radiomics. The population is randomly divided into a training group (672 cases) and an external verification group (288 cases) at a ratio of 7:3. The enhanced CTC (venous phase) image of the population in the training group is stored into a predetermined folder, and complete information is input in the clinical data acquisition module. In the embodiments of the present disclosure, a total of three most relevant radiomics features, compactness1, GLZM_ZP, and GLSZM_SAHGLE, are incorporated into the Sig1, and three radiomics features, GLZM_ZP, GLSZM_SAHGLE, and GlSZM_GrayLevel-NonUniformity are incorporated into the Sig2.

Figure 6:
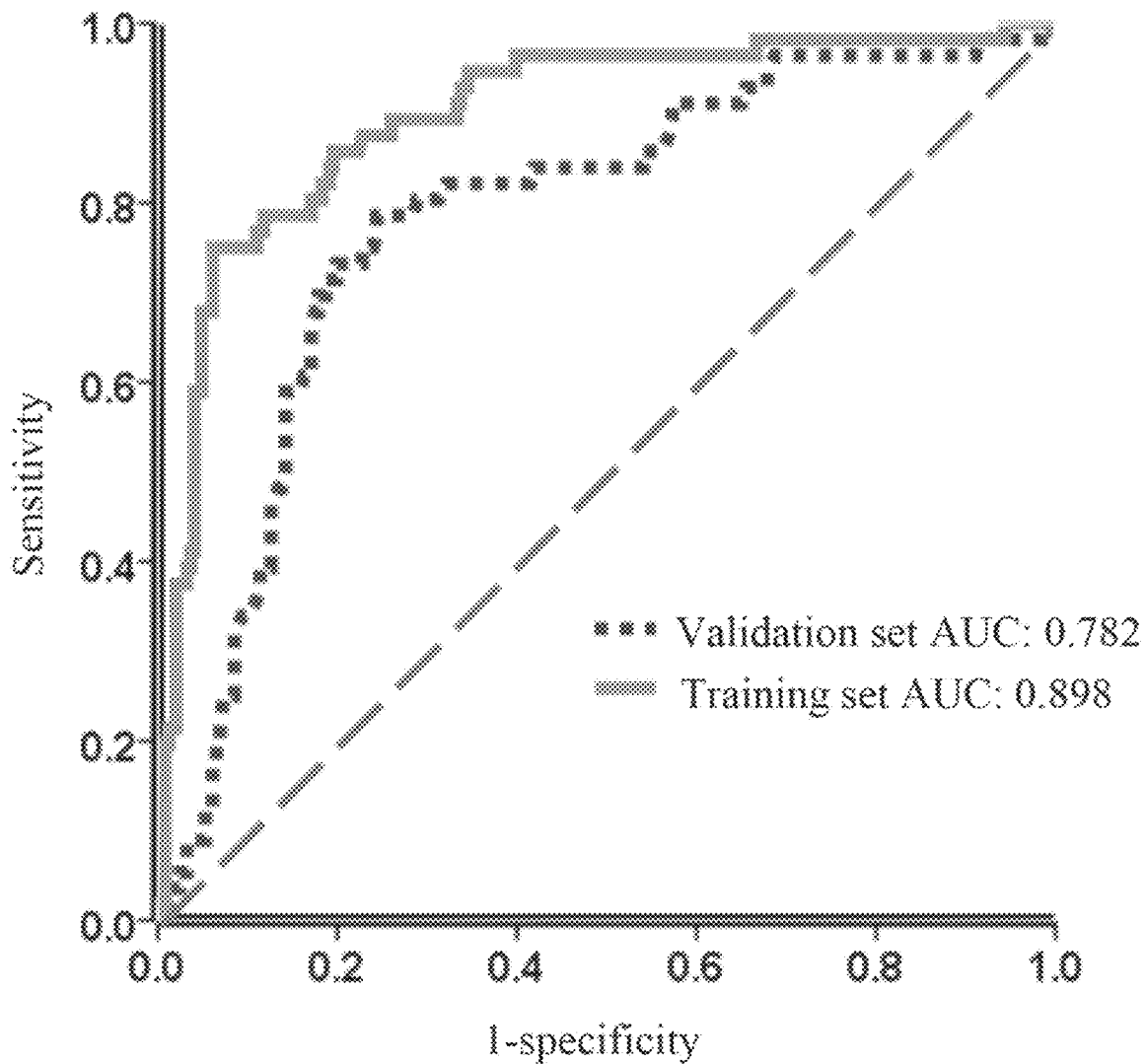
FIG. 6 is a schematic diagram of the prediction performance for cases of a training set and cases of a verification set in an embodiment of the present disclosure.

Referring to FIG. 6, it is a schematic diagram of the prediction performance on cases of a training set and cases of a verification set in the embodiments of the present disclosure. After the construction of an initial system model is completed, by sequentially storing the enhanced CTC (venous phase) image of the patient to be predicted (verification set) and inputting the clinical data (without pathological colonoscopy information), the system can conduct calculation based on the aforementioned nomogram, display the Sig1 and Sig2 signature scores, model 1 and model 2 scores of the specific patient according to the settings, and output a final diagnosis result (when the model 1 score is <75, the model 1 score and a malignant risk will be output; when the model 1 score is ≥75, the process will further proceed to model 2 calculation and output a model 2 score and a risk above T1N0). In the present embodiments, by taking the patient to be predicted as a verification case, after all the prediction results are obtained, the actual colonoscopy and pathological conditions of the patient are finally input into the system, and the consistency and stability of the model are evaluated according to the deviation between the predicted and actual conditions. As shown in FIG. 6, the prediction performance AUCs of the final output result of the system model on the cases of the training set and the cases of the verification set in the present embodiments reach 0.898 and 0.782, respectively.

In the present embodiments, by establishing a radiomics signature model; establishing a first classification comprehensive diagnosis model; establishing a second classification comprehensive diagnosis model; and constructing a radiomics signature-generation module, a benign and malignant comprehensive classification module, a malignant focus sub-classification module, a result displaying module and module connections based on the radiomics signature model, the first classification comprehensive diagnosis model and the second classification comprehensive diagnosis model, a system for performing semi-automatic diagnosis of colorectal tumors under supervision (manually delineating a focus instead of CAD automatic recognition) on a main basis of radiomics analysis of CT colonoscopy (CTC) combined with clinical information, is constructed. This system can not only identify the benign (a normal intestinal wall or hyperplastic polyps) and malignant (precancerous lesions or cancer) of suspicious lesions, but also further reclassify the malignant lesions (the precancerous lesions, the cancer below T1N0, and the staged cancer above T1N0), to help clinicians make further decisions.

Moreover, the embodiments of the present disclosure further provide a terminal device comprising a memory, a processor, and a tumor diagnosis system construction program stored in the memory and operable on the processor, wherein when executed by the processor, the tumor diagnosis system construction program implements the steps of the method for constructing a tumor diagnosis system as described above.

Since when executed by the processor, the present tumor diagnosis system construction program adopts all the technical solutions of all the aforementioned embodiments, it has at least all the beneficial effects brought by all the technical solutions of all the aforementioned embodiments, the description of which will not be repeated here one by one anymore.

Moreover, the embodiments of the present disclosure further provide a computer-readable storage medium on which a tumor diagnosis system construction program is stored, wherein when executed by a processor, the tumor diagnosis system construction program implements the steps of the method for constructing a tumor diagnosis system as described above.

Since when executed by the processor, the present tumor diagnosis system construction program adopts all the technical solutions of the aforementioned embodiments, it has at least all the beneficial effects brought by all the technical solutions of the aforementioned embodiments, the description of which will not be repeated here one by one anymore.

Compared with the prior art, for the tumor diagnosis system and a construction method thereof, an apparatus, a terminal device and a storage medium proposed in the embodiments of the present disclosure, by acquiring target radiomics information and clinical data information through a radiomics signature-generation module in the tumor diagnosis system, and obtaining a radiomics signature based on a pre-trained radiomics signature model and according to the target radiomics information and the clinical data information; generating a first classification comprehensive diagnosis result through a benign and malignant comprehensive classification module based on a pre-trained first classification comprehensive diagnosis model and based on a ambient situation of a lesion outside an intestinal wall, the clinical data information and the first radiomics signature; judging whether the first classification comprehensive diagnosis result includes high-risk malignant information through a malignant focus sub-classification module, and generating a second classification comprehensive diagnosis result based on a pre-trained second classification comprehensive diagnosis model and according to the ambient situation of the lesion outside the intestinal wall, the clinical data information and the second radiomics signature, if the first classification comprehensive diagnosis result includes the high-risk malignant information; and obtaining and displaying a final diagnosis result through a result displaying module, it achieves comprehensive diagnosis which combines radiomics and clinical information, which can not only identify the benign and malignant of suspicious lesions, but also further reclassify malignant lesions, so as to help clinicians make further decisions, without the need for colonoscopy in the whole process, thereby reducing the screening difficulty of colorectal tumors and improving the diagnostic effect on the colorectal tumors simultaneously.

It should be noted that, the terms "include", "comprise" or any other variations thereof described herein are intended to cover non-exclusive inclusion, so that a process, method, substance or system comprising a series of elements includes not only those elements, but also other elements not explicitly listed, or the elements inherent to such process, method, substance or system. Without further limitations, an element defined by the phrase "comprising a . . . " does not preclude the presence of additional identical elements in the process, method, article or system including that element.

The serial numbers of the aforementioned embodiments of the present application are only used for description, and do not represent the advantages and disadvantages of the embodiments.

Through the aforementioned description of embodiments, those skilled in the art can clearly understand that the methods of the aforementioned embodiments can be implemented by means of software plus a necessary general-purpose hardware platform, and of course also by hardware, but in many cases the former is a better implementation. Based on such understanding, the technical solution of the present application in nature or a part thereof that contributes to the prior art can be embodied in the form of a software product. The computer software product is stored in one of the aforementioned storage media (e.g. ROM/RAM, a magnetic disk, an optical disk), including several instructions to make a terminal device (which may be a mobile phone, a computer, a server, a controlled terminal, or a network device, etc.) to execute the method in each embodiment of the present application.

The above are only preferred embodiments of the present invention, but not intended to limit the protection scope of the present disclosure. Any equivalent structure or equivalent flow transformation made by using the contents of the specification of the present disclosure and the accompanying drawings, or direct or indirect uses in other related technical fields, are similarly included in the claimed patent scope of the present disclosure.

What is claimed is:

1. A tumor diagnosis system, comprising:
a plurality of modules, the modules comprising a computer executable code stored on a non-transitory computer-readable storage medium, the modules including:
a radiomics signature-generation module configured to perform acquiring target radiomics information and clinical data information, and obtaining a radiomics signature according to the target radiomics information and the clinical data information, based on a pre-trained radiomics signature model, wherein the radiomics signature comprises a first radiomics signature and a second radiomics signature;
a benign and malignant comprehensive classification module configured to perform acquiring an ambient situation of a lesion outside an intestinal wall, the clinical data information and the first radiomics signature, and generating a first classification comprehensive diagnosis result according to the ambient situation of the lesion outside the intestinal wall, the clinical data information and the first radiomics signature, based on a pre-trained first classification comprehensive diagnosis model;
a malignant focus sub-classification module configured to perform acquiring the first classification comprehensive diagnosis result from the benign and malignant comprehensive classification module, and judging whether the first classification comprehensive diagnosis result comprises high-risk malignant information, wherein if the first classification comprehensive diagnosis result comprises the high-risk malignant information, the ambient situation of the lesion outside the intestinal wall and the clinical data information are obtained from the benign and malignant comprehensive classification module, the second radiomics signature is obtained from the radiomics signature-generation module, and a second classification comprehensive diagnosis result is generated according to the ambient situation of the lesion outside the intestinal wall, the clinical data information and the second radiomics signature, based on a pre-trained second classification comprehensive diagnosis model;
a result displaying module configured to perform acquiring the first classification comprehensive diagnosis result and/or the second classification comprehensive diagnosis result, obtaining a final diagnosis result according to the first classification comprehensive diagnosis result and/or the second classification comprehensive diagnosis result, and displaying the final diagnosis result for a user to check;
a CT colonoscopy (CTC) image preprocessing and reconstructing module configured to perform acquiring an enhanced CTC image of a patient to be diagnosed, and standardizing signal strength and layer thickness of the CTC image through a filter to obtain a preprocessed CTC image, and reconstructing the preprocessed CTC image based on a virtual endoscopy post-processing technology to obtain CT virtual endoscopic imaging for the user to conduct focus localization on the virtual endoscopic imaging and further obtain a focus localization image; and acquiring the focus localization image, and generating a CTC tomographic image according to the focus localization image;

a lesion marking module configured to perform acquiring the CTC tomographic image, recording the ambient situation of the lesion outside the intestinal wall according to the CTC tomographic image, and sending the ambient situation of the lesion outside the intestinal wall to the benign and malignant comprehensive classification module; providing the CTC tomographic image to the user for the user to delineate the CTC tomographic image layer by layer to obtain a region of interest; and acquiring the region of interest and sending the region of interest to a radiomics feature extraction module;

the radiomics feature extraction module configured to perform feature extraction on the region of interest to obtain the target radiomics information, and send the target radiomics information to the radiomics signature-generation module;

a clinical data acquisition module configured to perform acquiring the clinical data information of the patient to be diagnosed input by the user, and sending the clinical data information to the radiomics signature-generation module, wherein the clinical data information comprises one or more of a gender, age, body mass index, family history of cancer, smoking history, constipation history, fecal occult blood and serological test result;

wherein the clinical data acquisition module further comprises a training sample data acquisition unit, the training sample data acquisition unit is used for acquiring training sample data information input by the user and sending the training sample data information to a radiomics signature model training module, wherein the training sample data information comprises clinical data information, colonoscopy and pathological information of a training set;

wherein in the tumor diagnosis system, the radiomics signature model training module comprises a data cleaning unit, a logistic regression unit, and a signature vector calculation unit, wherein the data cleaning unit is used for acquiring an omics feature value and the training sample data information, and performing data cleaning on the omics feature value and the training sample data information to obtain cleaned multi-omics feature data;

the logistic regression unit is used for performing dimensionality reduction screening on the cleaned multi-omics feature data to obtain a first relevant radiomics feature and a second relevant radiomics feature; and the signature vector calculation unit is used for incorporating the first relevant radiomics feature and the second relevant radiomics feature into a vector formula to obtain the radiomics signature model;

a first classification comprehensive diagnosis model training module configured to perform acquiring the training sample data information and the ambient situation of the lesion outside the intestinal wall of the training set, performing screening and analysis according to the training sample data information and the ambient situation of the lesion outside the intestinal wall of the training set to obtain a clinical risk factor; and performing training according to the clinical risk factor through a model training method to obtain the first classification comprehensive diagnosis model; and a second classification comprehensive diagnosis model training module configured to perform judging whether the first classification comprehensive diagnosis result of the training set generated by the first classification comprehensive diagnosis model comprises the high-risk malignant information, wherein if the first classification comprehensive diagnosis result of the training set comprises the high-risk malignant information, the training sample data information and the ambient situation of the lesion outside the intestinal wall of the training set are acquired from the first classification comprehensive diagnosis model training module, and training is conducted in connection with a classification criteria according to the training sample data information and the ambient situation of the lesion outside the intestinal wall of the training set to obtain the second classification comprehensive diagnosis model.

2. A method for constructing the tumor diagnosis system according to claim 1, comprising:
   constructing a radiomics signature-generation module based on a pre-trained radiomics signature model;
   constructing a benign and malignant comprehensive classification module based on a pre-trained first classification comprehensive diagnosis model;
   constructing a malignant focus sub-classification module based on a pre-trained second classification comprehensive diagnosis model; and
   constructing a result displaying module, a CTC image preprocessing and reconstructing module, and a lesion marking module, and constructing the tumor diagnosis system based on the radiomics signature-generation module, the benign and malignant comprehensive classification module, the malignant focus sub-classification module and the result displaying module.

3. The method for constructing the tumor diagnosis system according to claim 2, wherein before the step of constructing the radiomics signature-generation module based on the pre-trained radiomics signature model, the method further comprises:
   acquiring an omics feature value and training sample data information;
   performing data cleaning on the omics feature value and the training sample data information to obtain cleaned multi-omics feature data;
   performing dimensionality reduction screening on the cleaned multi-omics feature data to obtain a first relevant radiomics feature and a second relevant radiomics feature; and
   incorporating the first relevant radiomics feature and the second relevant radiomics feature into a vector formula to obtain the radiomics signature model.

4. The method for constructing the tumor diagnosis system according to claim 3, wherein before the step of constructing the benign and malignant comprehensive classification module based on the pre-trained first classification comprehensive diagnosis model, the method further comprises:
   acquiring the training sample data information and the ambient situation of a lesion outside an intestinal wall of a training set;
   performing screening and analysis according to the training sample data information and the ambient situation of the lesion outside the intestinal wall of the training set to obtain a clinical risk factor; and
   performing model training according to the clinical risk factor through a model training method to obtain the first classification comprehensive diagnosis model, wherein the model training method comprises Decision Tree, Random Forest, Support Vector Machines, and Naive Bayes.

5. The method for constructing the tumor diagnosis system according to claim 3, wherein before the step of constructing the malignant focus sub-classification module based on the pre-trained second classification comprehensive diagnosis model, the method further comprises:

judging whether the first classification comprehensive diagnosis result of a training set generated by the first classification comprehensive diagnosis model comprises high-risk malignant information; and acquiring the training sample data information and the ambient situation of the lesion outside the intestinal wall of the training set, if the first classification comprehensive diagnosis result of the training set comprises the high-risk malignant information, and training, in connection with a classification criteria, according to the training sample data information and the ambient situation of the lesion outside the intestinal wall of the training set, to obtain the second classification comprehensive diagnosis model.

* * * * *